United States Patent [19]

Payne et al.

[11] Patent Number: 5,298,245
[45] Date of Patent: Mar. 29, 1994

[54] BACILLUS THURINGIENSIS ISOLATES ACTIVE AGAINST DIPTERAN PESTS

[75] Inventors: Jewel M. Payne; Kendrick A. Uyeda, both of San Diego; Christine J. Stalder, La Mesa; Tracy E. Michaels, Escondido, all of Calif.

[73] Assignee: Mycogen Corporation, San Diego, Calif.

[21] Appl. No.: 746,751

[22] Filed: Aug. 21, 1991

Related U.S. Application Data

[63] Continuation-in-part of Ser. No. 708,266, May 28, 1991, abandoned, which is a continuation-in-part of Ser. No. 647,399, Jan. 29, 1991, abandoned.

[51] Int. Cl.$^5$ .................... A01N 63/00; A61K 37/00; C12N 1/20; C12N 1/12
[52] U.S. Cl. ................................ 424/936; 424/93 K; 435/252.1; 435/252.5; 435/832
[58] Field of Search .................. 435/832, 252.1, 252.5; 424/93 L, 93 K

[56] References Cited

U.S. PATENT DOCUMENTS

| | | | |
|---|---|---|---|
| 3,086,922 | 4/1963 | Mechalas et al. | 424/93 L |
| 4,609,550 | 9/1986 | Fitz-James | 424/93 L |

FOREIGN PATENT DOCUMENTS

| | | | |
|---|---|---|---|
| 0228228 | 7/1987 | European Pat. Off. | 424/93 L |
| 0409438 | 7/1990 | European Pat. Off. | |
| 903070204.9 | 7/1990 | European Pat. Off. | |
| 1121806 | 7/1986 | U.S.S.R. | 424/93 L |

OTHER PUBLICATIONS

Couch, T. L., (1980) "Mosquito Pathogenicity of *Bacillus thuringiensis* var. *israelensis*", Developments in Industrial Microbiology 22:61–76.
Beegle, C. C.. (1978) "Use of Entomogenous Bacteria in Agroecosystems", Developments in Industrial Microbiology 20:97–104.
Goldberg, L. J., J. Margalit (1977) Mosquito New 37: 355–358.
Metcalf, C. and W. Flint (1962) *Destructive and Useful Insects*, McGraw–Hill Book Co., N.Y., pp. 1030–1035.
Parrella, M. P. (1987) Biology of Liriomyza. Ann. Rev. of Entomology. 32:201–224.
Hespenheide, H. A. (1991) Bionomics of leafmining insects. Ann. Rev. Entomology. 36:535–560.
Padua, L. E., M. Ohba, K. Aizawa (1984) J. Invertebrate Pathology 44:12–17.
Mulla, M. S., B. A. Federici, H. A. Darwazeh (1982) Environmental Entomology 11:788–795.
Temeyer, K. B. (1990) "Potential of *Bacillus thuringiensis* for Fly Control", Fifth International Colloquium on Invertebrate Pathology and Microbial Control, Society for Invertebrate Pathology, 352–356.
Hofte, Herman, and H. R. Whiteley (1989) "Insecticidal Crystal Proteins of *Bacillus thuringiensis*" Microbiological Reviews 53(2):242–255.
Donovan, William P., Cathy Dankocsik, and M. Pearce Gilbert (1988) "Molecular Characterization of Gene Encoding a 72-Kilodalton Mosquito-Toxic Crystal Protein from *Bacillus thuringiensis* subsp. *israelensis*" Journal of Bacteriology 170(10):4732–4738.
Sekar, Vaithilingam (1986) "Biochemical and Immunological Characterization of the Cloned Crystal Toxin of *Bacillus thuringiensis* var. *israelensis*" Biochemical and Biophysical Research Communications 137(2):748–751.
Drobniewski, Francis A., and David J. Ellar (1989) "Purification and Properties of a 28-Kilodalton Hemolytic and Mosquitocidal Protein Toxin of *Bacillus thuringiensis* subsp. *darmstadiensis* 73E-10-2" Journal of Bacteriology 177(6):3060–3067.

*Primary Examiner*—David M. Naff
*Assistant Examiner*—L. Blaine Lankford
*Attorney, Agent, or Firm*—Saliwanchik & Saliwanchik

[57] ABSTRACT

*Bacillus thuringiensis* cultures deposited as NRRL B-18747, NRRL B-18749 and NRRL B-18750 have dipteran activity. Thus, these cultures, or mutants thereof, can be used to control such insect pests. Further, genes encoding novel δ-endotoxins can be removed from these cultures and transferred to other host microbes, or plants. Expression of the δ-endotoxins in such hosts results in the control of susceptible insect pests in the environment of such hosts.

19 Claims, 1 Drawing Sheet

A. Protein standard
B. *B.t.* PS192N1
C. *B.t.* PS123D1
D. *B.t.* PS71M3
E. Protein standard
F. *B.t.* PS201T6
G. *B.t.* PS201L1
H. *B.t.* PS196S1
I. *B.t.* PS92J
J. Protein standard

BACILLUS THURINGIENSIS ISOLATES ACTIVE AGAINST DIPTERAN PESTS

CROSS-REFERENCE TO A RELATED APPLICATION

This is a continuation-in-part of co-pending U.S. application Ser. No. 07/708,266 filed May 28, 1991, now abandoned, which is a continuation-in-part application of co-pending U.S. application Ser. No. 07/647,399 filed Jan. 29, 1991 abandoned.

BACKGROUND OF THE INVENTION

Many hundreds of strains of *Bacillus thuringiensis* (*B.t.*) produce insecticidal toxins designated as delta endotoxins. They are synthesized by sporulating *B.t.* cells. When toxin is ingested by a susceptible insect, the cells of the gut epithelium are destroyed.

The reported activity spectrum of *B.t.* covers insect species within the orders Lepidoptera and Coleoptera, many of which are major pests in agriculture and forestry. The activity spectrum also includes the insect order Diptera, which includes mosquitoes and black flies. See Couch, T. L. (1980) "Mosquito Pathogenicity of *Bacillus thuringiensis* var. *israelensis*," Developments in Industrial Microbiology 22:61-76; Beegle, C.C. (1978) "Use of Entomogenous Bacteria in Agroecosystems," Developments in Industrial Microbiology 20:97-104. Dipteran insects are serious nuisances as well as being vectors of many serious human and animal diseases such as malaria, onchocerciasis, equine encephalitis, and dog heartworm.

The two varieties of *B.t.* known to kill mosquitos and blackflies are *B.t. israelensis* (*B.t.i.*) (Goldberg, L.J., J. Margalit [1977] Mosquito News 37:355-358) and *B.t. morrisoni* (*B.t.m.*) (Padua, L.E., M. Ohba, K. Aizawa [1984] J. Invertebrate Pathology 44:12-17). These are not harmful to non-target organisms (Mulla, M. S., B. A. Federici, H. A. Darwazeh [1982] Environmental Entomology 11:788-795), and play an important role in the integrated management of dipteran pests. They are safe to use in urban areas, and can be used in aquatic environments without harm to other species.

Dipteran pests are also a major problem in the poultry and cattle industries. The horn fly, a serious cattle pest, is killed by *B.t.* in the larval stages (Temeyer, K.B. [1990] "Potential of *Bacillus thuringiensis* for fly control," Fifth International Colloquium on Invertebrate Pathology and Microbial Control, Society for Invertebrate Pathology, 352-356). European Patent Application 90307204.9 (Publication No. 0 409 438) discloses *Bacillus thuringiensis* dipteran-active isolates PS71M3 and PS123D1.

Flies are an abundant species that can be found almost everywhere. They usually occur in such large numbers as to constitute a nuisance. The majority of the Diptera are considered pests and are of economic importance. A number of adult species are blood-sucking and cause irritation to man and his domestic animals. Others are scavenging flies that mechanically transmit organisms and pathogens that contaminate food. Both types of flies are important vectors of disease, such as malaria, yellow fever, filariasis, sleeping sickness, typhoid fever, and dysentery. Larvae of a few species are pests of major agriculture crops. The larvae can feed on all parts of the plant such as seeds, roots, leaves and fruits. Larvae of certain species feed on fungus causing damage to mushroom production. Larvae can irritate domestic animals when they develop in the animal. Both the adults and larvae are considered pests to man and agriculture.

House flies (family Muscidae) are an important pest from the order Diptera. They are considered a nuisance and are vectors of human and animal diseases. Their habits of walking and feeding on garbage and excrement and on the human person and food make them ideal agents for the transfer of disease organisms (Metcalf, C. and Flint, W. 1962. *Destructive and Useful Insects*, McGraw-Hill Book Co., N.Y., pp. 1030-1035.). This species can also be a pest to animals and transmit disease through open wounds. Muscidae also include the little house fly, face fly, stable fly, and horn fly, all of which are pests of livestock. These species are pests of cattle, poultry, horses and other types of livestock. They breed in manure and decaying straw located near the animals. The horn and stable flies are biting flies which cause stress to dairy cattle reducing milk production. The family Muscidae is considered an economic problem domestically and worldwide.

Leafmining flies cause damage and yield loss to economically important crops such as potatoes, tomatoes and celery. Dipteran leafminers are also considered a major pest in the ornamental flower industry (Parrella, M. P. 1987. Biology of Liriomyza. Ann. Rev. Entomol. 32:201-224). The most common leafminers are found in the family Agromyzidae although the families Anthomyiidae, Drosophilidae and Ephydridae also contain leafmining flies (Hespenheide, H. A. 1991. Bionomics of leafmining insects. Ann. Rev. Entomolo. 36:535-60). Flies in the genus Liriomyza (also known as serpentine leafminers) are particularly important because of their worldwide distribution, polyphagous nature and resistance to insecticides. In the state of California, the chrysanthemum industry lost approximately 93 million dollars to *Liriomyza trifolii* between the years of 1981-1985.

There are also dipteran pests of plants, such as Hessian fly, Medfly, and Mexfly, for which a *B.t.* product would be very valuable.

Brief Summary of the Invention

The subject invention concerns novel *Bacillus thuringiensis* isolates which have activity against dipteran pests. Specifically, *Bacillus thuringiensis* isolates have been found to be toxic to the Yellow Fever mosquito, *Aedes aegypti*, House fly, *Musca domestica*, and Leafmining flies *Liriomyza trifolii*.

More specifically, the invention comprises novel *B.t.* isolates designated *B.t.* PS92J, *B.t.* PS196S1, *B.t.* PS201L1, and *B.t.* PS201T6, and mutants thereof, and novel delta endotoxin genes obtainable from these *B.t.* isolates which encode proteins which are active against dipteran pests.

The *Bacillus thuringiensis* isolate or toxins therefrom can be utilized as a spray for litter, manure, water, plant and other surfaces. They could also be used as a feed through for domesticated animals and livestock. Transgenic plants and seeds could be used for control of stem, leaf, and seed feeding maggots. Seeds could also be treated with a slurry of the isolate or toxin therefrom.

DETAILED DISCLOSURE OF THE INVENTION

Figure 1:
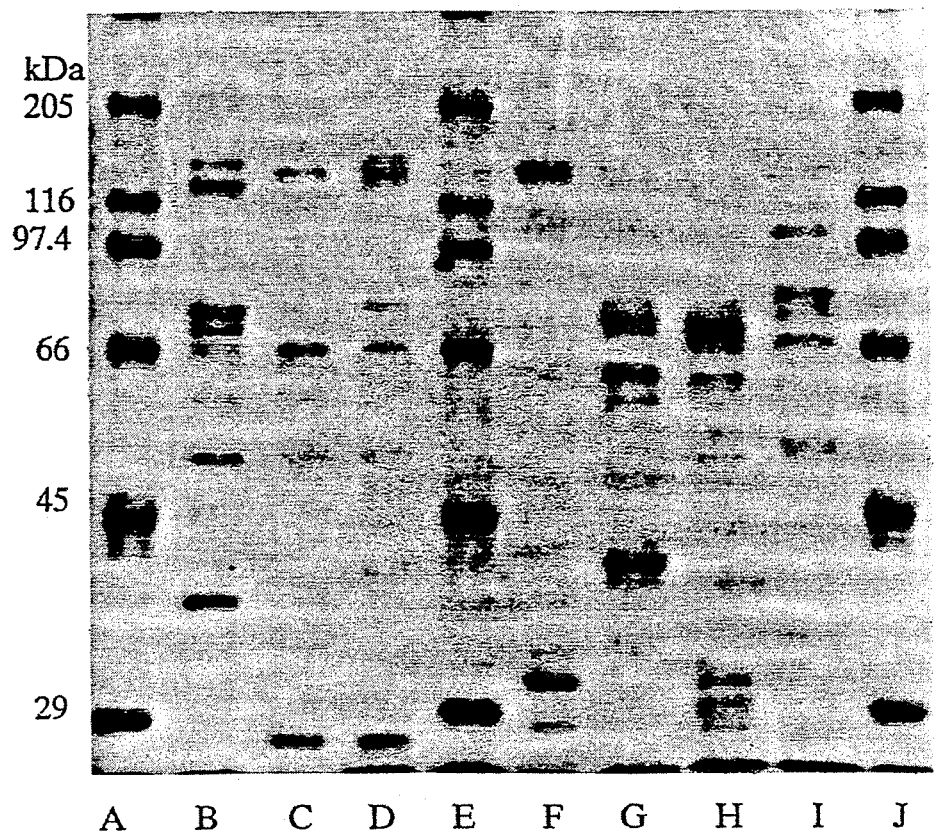
FIG. 1 is a photograph of a standard SDS polyacrylamide gel showing alkali-soluble proteins of mosquito-active *B.t.* strains.

The novel *Bacillus thuringiensis* isolates of the subject invention have the following characteristics:

Characteristics Shared by *B.t.* PS92J, *B.t.* PS196S1, *B.t.* PS201L1, and *B.t.* PS201T6

Colony morphology—large colony, dull surface, typical *B.t.*
Vegetative cell morphology—typical *B.t.*
Culture methods—typical for *B.t.*
Insecticidal activity—inclusions kill *Aedes aegypti*

| Characteristics Distinguishing *B.t.* PS92J, *B.t.* PS196S1, *B.t.* PS201L1, and *B.t.* PS201T6 From Each Other and From Known Mosquito-Active Strains | | | |
|---|---|---|---|
| | Serovar | Inclusion | Protein sizes (kDa) |
| Known Strains | | | |
| *B.t.* PS71M3 | 8a8b, *morrisoni* | amorphic | 142, 133 doublet, 67, 27 |
| *B.t.* PS123D1 | 14, *israelensis* | amorphic | 133, 67, 27 |
| *B.t.* PS192N1 (NRRL B-18721) | 19, *tochigiensis* | amorphic | 140, 122, 76, 72, 38 |
| New Strains | | | |
| *B.t.* PS92J | new serovar | amorphic | 102, 81, 67 |
| *B.t.* PS196S1 | 10, *darmstadiensis* | amorphic | 73, 69, 29 |
| *B.t.* PS201L1 | no reaction | amorphic | 75 triplet, 62, 40 |
| *B.t.* PS201T6 | 24, *neoleonensis* | elliptical & bipyramidal | 133, 31 |

The novel *B.t.* isolates of the invention, and mutants thereof, can be cultured using standard known media and fermentation techniques. Upon completion of the fermentation cycle, the bacteria can be harvested by first separating the *B.t.* spores and crystals from the fermentation broth by means well known in the art. The recovered *B.t.* spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains. The novel *B.t.* isolates, and mutants thereof, can be used to control dipteran pests.

The cultures of the subject invention were deposited in the Agricultural Research Service Patent Culture Collection (NRRL), Northern Regional Research Center, 1815 North University Street, Peoria, Ill. 61604 USA.

| Culture | Accession No. | Deposit date |
|---|---|---|
| *Bacillus thuringiensis* PS92J | NRRL B-18747 | January 9, 1991 |
| *Bacillus thuringiensis* PS196S1 | NRRL B-18748 | January 9, 1991 |
| *Bacillus thuringiensis* PS201L1 | NRRL B-18749 | January 9, 1991 |
| *Bacillus thuringiensis* PS201T6 | NRRL B-18750 | January 9, 1991 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. These deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the data of deposit or for the enforceable life of any patent which may issue disclosing a culture. The depositor acknowledges the duty to replace a deposit should the depository be unable to furnish a sample when requested, due to the condition of a deposit. All restrictions on the availability to the public of the subject culture deposits will be irrevocably removed upon the granting of a patent disclosing them.

The toxin genes harbored by the novel isolates of the subject invention can can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of dipteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the *B.t.* toxin.

Where the *B.t.* toxin gene is introduced via a suitable vector into a microbial host, and said host is applied to the environment in a living state, it is essential that certain host microbes be used. Microorganism hosts are selected which are known to occupy the "phytosphere" or aquatic environment. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves), and/or the rhizosphere (the soil surrounding plant roots), and/or aquatic environments. These microorganisms include bacteria, algae, and fungi. Of particular interest are microorganisms, such as bacteria, e.g., genera Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, Alcaligenes and Clostridium; fungi, particularly yeast, e.g., genera Saccharomyces, Cryptococcus, Kluyveromyces, Sprobolomyces, Rhodotorula, and Aureobasidium; microalgae, e.g., families Cyanophyceae, Prochlorophyceae, Rhodophyceae, Dinophyceae, Chrysophyceae, Prymnesiophyceae, Xanthophyceae, Raphidophceae, Bacillariophyceae, Eustigmatophyceae, Cryptophyceae, Euglenophyceae, Prasinophyceae, and Chlorophyceae. Of particular interest are such phytosphere bacterial species as *Pseudomonas syringae*, *Pseudomonas fluorescens*, *Serratia mar-* cescens, Acetobacter xylinum, Agrobacterium tumefaciens, Rhodopseudomonas spheroides, Xanthomonas campestris, Rhizobium melioti, Alcaligenes entrophus, and Azotobacter vinlandii; and phytosphere yeast species such as Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae, and Aureobasidium pollulans. Of particular interest are the pigmented microorganisms.

A wide variety of ways are available for introducing a B.t. gene expressing a toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transrciptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop condon(s), a terminator region, and optionally, a polyadenylation signal. A hydrophobic "leader" sequence may be employed at the amino terminus of the translated polypeptide sequence in order to promote secretion of the protein across the inner membrane.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 5000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The B.t. gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and-positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae, Actinomycetales, and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., Streptomyces sp., and the like. Specific organisms include *Pseudomonas aeruginosa, Pseudomonas fluorescens, Saccharomyces cerevisiae, Bacillus thuringiensis, Escherichia coli, Bacillus subtilis, Streptomyces lividans* and the like.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohol, such as isopropyl and ethanol; various histologic fixatives, such as Lugol iodine, Bouin's fixative, and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the dipteran pest(s), e.g., plants, soil or water, by spraying, dusting, sprinkling, or the like.

Mutants of the novel isolates of the invention can be made by procedures well known in the art. For example, an asporogenous mutant can be obtained through ethylmethane sulfonate (EMS) mutagenesis of a novel isolate. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture portions are by volume unless otherwise noted.

Example 1

Culturing of the Novel *B.t.* Isolates

A subculture of the novel *B.t.* isolates, or mutants thereof, can be used to inoculate the following medium, a peptone, glucose, salts medium.

| Bacto Peptone | 7.5 g/l |
|---|---|
| Glucose | 1.0 g/l |
| KH$_2$PO$_4$ | 3.4 g/l |
| K$_2$HPO$_4$ | 4.35 g/l |
| Salt Solution | 5.0 ml/l |
| CaCl$_2$ Solution | 5.0 ml/l |
| Salts Solution (100 ml) | |
| MgSO$_4$.7H$_2$O | 2.46 g |
| MnSO$_4$.H$_2$O | 0.04 g |
| ZnSO$_4$.7H$_2$O | 0.28 g |
| FeSO$_4$.7H$_2$O | 0.40 g |

-continued

| CaCl$_2$ Solution (100 ml) | |
|---|---|
| CaCl$_2$.2H$_2$O | 3.66 g |
| pH 7.2 | |

The salts solution and CaCl$_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The *B.t.* spores and/or crystals, obtained in the above fermentation, can be isolated by procedures well known in the art. A frequently-used procedure is to subject the harvested fermentation broth to separation techniques, e.g., centrifugation.

Example 2

Purification of protein

The *B. thuringiensis* isolate was cultured as described in Example 1. the parasporal inclusion bodies (toxin crystals) were partially purified by sodium bromide (26–40%) isopycnic gradient centrifugation (Pfannestiel, M.A., E. J. Ross, V. C. Kramer, and K. W. Nickerson [1984] FEMS Microbiol. Lett. 21:39).

Example 3

Activity of *B.t.* isolate against House Fly *Musca domestica*

Twenty grams of house fly media (Bioserve, Inc., Frenchtown, N.J.) was mixed with approximately 6 mg. PS201T6 toxin crystals per 50 ml of water. Ten 1st instar larvae were placed in a plastic 6 oz. cup with the diet/toxin preparation and covered with a paper towel. The bioassay was held in an incubator at 27° C. and evaluated for puparium formation.

| Toxicity of *Bacillus thuringiensis* Crystals to the 1st instar house fly | |
|---|---|
| *B.t.* isolate | Percent to form puparium (S.D) |
| PS201T6 | 0% |
| Control | 97% ± 5 |

Example 4

Activity Against Housefly Adults

The *B.t.* isolate, PS201T6, was tested against housefly adults. Gradient purified delta-endotoxin from 201T6 was suspended in a 10% sucrose solution at a rate of 2 mg/ml. The resulting mixture was used to saturate a dental wick placed in a clear plastic cup. Ten flies were added to the cup. Mortality was assessed 24 hours post-treatment. PS201T6 caused 100% mortality to the house fly, *Musca domestica*. Control experiments using water showed no mortality.

Example 5

Activity of *B.t.* Isolates Against *Aedes aegypti*

*Aedes aegypti*, the yellow fever mosquito, is used as an indicator of mosquito activity. The bioassay is performed on a spore and crystal suspension or a suspension of purified crystals. Dilutions of the suspension are added to water in a small cup. Third instar larvae are added, and mortality is read after 48 hours.

All of the novel isolates of the invention are active against *Aedes aegypti*.

Example 6

Activity of B.t. isolates to leafminers

The *B.t.* isolates, PS201T6, PS201L1, PS196S1 and PS92J were grown using standard techniques. Second instar larvae were allowed to feed on broths ad lib. All four isolates were toxic to the leafminer, *Liriomyza trifolii*.

Example 7

Insertion of Toxin Genes Into Plants

The novel genes, obtainable from the novel *B.t.* isolates of the invention, coding for the novel insecticidal toxin, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J [1983] Cell 32:1033–1043). A particularly useful vector in this regard is pEND4K (Klee, H. J., Yanofsky, M. F. and Nester, E. W. [1985] Bio/Technology 3:637–642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

Example 8

Cloning of Novel B. thuringiensis Genes Into Baculoviruses

The novel genes, obtainable from the novel *B.t.* isolates of the invention, can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399–406), and pAC380, described by Smith et al. (Smith, G. E., Summers, M. D. and Fraser, M. J. [1983] Mol Cell. Biol. 3:2156–2165). The gene coding for the novel protein toxin can be modified with BamHI linker s at appropriate regions both upstream and downstream from the coding region and inserted into the passenger site of one of the AcNPV vectors.

We claim:

1. A process for controlling dipterm insect pests which comprises contacting said insect pests with an insect-controlling effective amount of a microbe selected from the group consisting of *Bacillus thuringiensis* PS92J, having all the identifying characteristics of deposit NRRL B-18747; *Bacillus thuringiensis* PS196S1, having all the identifying characteristics of deposite NRRL B-18748; *Bacillus thuringiensis* PS201L1, having all the identifying characteristics of deposit NRRL B-18749; and *Bacillus thuringiensis* PS201T6, having all the identifying characteristics of deposit NRRL B-18750.

2. The process, according to claim 1, wherein said microbe is *Bacillus thuringiensis* PS92J.

3. The process, according to claim 1, wherein said microbe is *Bacillus thuringiensis* PS196S1.

4. The process, according to claim 1, wherein said microbe is *Bacillus thuringiensis* PS201L1.

5. The process, according to claim 1, wherein said microbe is *Bacillus thuringiensis* PS201T6.

6. The process, according to claim 1, wherein said insect pests are mosquitoes.

7. The process, according to claim 1, wherein said insect pest is the House fly larvae.

8. The process, according to claim 1, wherein said insect pest is the leafmining fly.

9. The process, according to claim 6, wherein said mosquitoes are selected from the group consisting of *Aedes aegypti*, *Aedes dorsalis*, *Anopheles albomanis*, *Culex pipiens quinquefasciatus*, and *Culex tarsalis*.

10. A composition of matter comprising a *Bacillus thuringiensis* selected from the group consisting of *Bacillus thuringiensis* PS92J, having all the identifying characteristics of deposit NRRL B-18747; *Bacillus thuringiensis* PS196S1, having all the identifying characteristics of deposit NRRL B-18748; *Bacillus thuringiensis* PS201L1, having all the identifying characteristics of deposit NRRL B-18749; and *Bacillus thuringiensis* PS201T6, having all the identifying characteristics of deposit NRRL B-18750, in association with an insecticide carrier.

11. A composition of matter, according to claim 10, wherein said *Bacillus thuringiensis* is *Bacillus thuringiensis* PS92J.

12. A composition of matter, according to claim 10, wherein said *Bacillus thuringiensis* is *Bacillus thuringiensis* PS196S1.

13. A composition of matter, according to claim 10, wherein said *Bacillus thuringiensis* is *Bacillus thuringiensis* PS201L1.

14. A composition of matter, according to claim 10, wherein said *Bacillus thuringiensis* is *Bacillus thuringiensis* PS201T6.

15. A biologically pure culture selected from the group consisting of *Bacillus thuringiensis* PS92J, having all the identifying characteristics of deposit NRRL B-18747; *Bacillus thuringiensis* PS196S1, having all the identifying characteristics of deposit NRRL B-18748; *Bacillus thuringiensis* PS201L1, having all the identifying characteristics of deposit NRRL B-18749; and *Bacillus thuringiensis* PS201T6, having all the identifying characteristics of deposit NRRL B-18750.

16. The biologically pure culture, according to claim 15, wherein said isolate is *Bacillus thuringiensis* PS92J, having all the identifying characteristics of deposit NRRL B-18747.

17. The biologically pure culture, according to claim 15, wherein said isolate is *Bacillus thuringiensis* PS196S1, having all the identifying characteristics of deposit NRRL B-18748.

18. The biologically pure culture, according to claim 15, wherein said isolate is *Bacillus thuringiensis* PS201L1, having all the identifying characteristics of deposit NRRL B-18749.

19. The biologically pure culture, according to claim 15, wherein said isolate is *Bacillus thuringiensis* PS201T6, having all the identifying characteristics of deposit NRRL B-18750.

* * * * *

UNITED STATES PATENT AND TRADEMARK OFFICE
CERTIFICATE OF CORRECTION

PATENT NO.   :   5,298,245

DATED        :   March 29, 1994

INVENTOR(S)  :   Payne *et al.*

It is certified that error appears in the above-identified patent and that said Letters Patent is hereby corrected as shown below:

Column 11, line 56: Delete "controlling dipterm" insert -- controlling dipteran --.
Column 11, line 62: Delete "of deposite" insert -- of deposit --.
Column 12, line 52: Delete "isolate is" insert -- culture is --.
Column 12, line 56: Delete "isolate is" insert -- culture is --.
Column 12, line 60: Delete "isolate is" insert -- culture is --.
Column 12, line 64: Delete "isolate is" insert -- culture is --.

Column 4, line 12: Delete "the data of" insert -- the date of --.
Column 4, line 64: Delete "Raphidophceae" insert -- Raphidophyceae --.
Column 8, line 15-16: Delete "alcohol," insert -- alcohols, --.
Column 9, line 25: Delete "plated over the" insert -- plated directly over the --.
Column 11, line 50: Delete "BamHI linker s at" insert -- <u>BamHI</u> linkers at --.
Abstract, line 2: Delete "18747, NRRL B-18749" insert -- 18747, NRRL B-18748, NRRL B-18749 --.

Signed and Sealed this

Sixth Day of September, 1994

*Attest:*

BRUCE LEHMAN

*Attesting Officer*    *Commissioner of Patents and Trademarks*